(12) United States Patent
Shi et al.

(10) Patent No.: US 9,968,717 B2
(45) Date of Patent: May 15, 2018

(54) SCAFFOLD WITH DRUG COATING FOR TREATING RESTENOSIS AND PREPARATION METHOD THEREOF

(71) Applicant: XIYUAN HOSPITAL OF CHINA ACADEMY OF CHINESE MEDICAL SCIENCES, Beijing (CN)

(72) Inventors: Dazhuo Shi, Beijing (CN); Jiangang Liu, Beijing (CN); Fuhai Zhao, Beijing (CN); Xin Wang, Beijing (CN); Dawu Zhang, Beijing (CN); Peili Wang, Beijing (CN); Jianpeng Du, Beijing (CN); Yuanyuan Cui, Beijing (CN); Lei Zhang, Beijing (CN); Kai Cui, Beijing (CN); Zhengcai Zhang, Beijing (CN)

(73) Assignee: Xiyuan Hospital of China Academy of Chinese Medical Sciences, Beijing (CN)

( * ) Notice: Subject to any disclaimer, the term of this patent is extended or adjusted under 35 U.S.C. 154(b) by 0 days. days.

(21) Appl. No.: 15/313,913

(22) PCT Filed: Apr. 20, 2015

(86) PCT No.: PCT/CN2015/076946
§ 371 (c)(1),
(2) Date: Nov. 23, 2016

(87) PCT Pub. No.: WO2015/180541
PCT Pub. Date: Dec. 3, 2015

(65) Prior Publication Data
US 2017/0216497 A1    Aug. 3, 2017

(30) Foreign Application Priority Data

May 28, 2014    (CN) .......................... 2014 1 02325900

(51) Int. Cl.
| | |
|---|---|
| *A61L 31/16* | (2006.01) |
| *A61F 2/89* | (2013.01) |
| *A61L 31/08* | (2006.01) |
| *A61L 31/02* | (2006.01) |
| *A61L 31/14* | (2006.01) |

(52) U.S. Cl.
CPC ................ *A61L 31/16* (2013.01); *A61F 2/89* (2013.01); *A61L 31/022* (2013.01); *A61L 31/08* (2013.01); *A61L 31/146* (2013.01); *A61L 2300/416* (2013.01); *A61L 2420/02* (2013.01)

(58) Field of Classification Search
CPC .... A61L 31/08; A61L 31/16; A61L 2300/416; A61L 2420/02; A61L 31/022; A61L 31/146; A61F 2/82; A61F 2/89
See application file for complete search history.

(56) References Cited

U.S. PATENT DOCUMENTS

2010/0215833 A1* 8/2010 Sellin ........................ A61F 2/06
427/2.25

FOREIGN PATENT DOCUMENTS

CN         100441155 C   * 12/2008

OTHER PUBLICATIONS

Buccheri et al (Journal of Thoracic Disease, 2016, vol. 8, pp. E1150-E1162).*
Zhong et al (CN 100441155 C published in Dec. 2008, English translation on Google downloaded on Sep. 25, 2017).*

* cited by examiner

*Primary Examiner* — Mark V Stevens
(74) *Attorney, Agent, or Firm* — Ladas & Parry LLP

(57) ABSTRACT

Disclosed is a stent with a drug coating for preventing and treating restenosis, comprising a stent and a drug coating covering the surface of the stent. The active ingredients in the drug coating are guaiane sesquiterpene compounds P1, P2 and P3. P1 is Zedoalactone B, P2 is a stereoisomer of P1, and P3 is Zedoarondiol. Compared with an existing sirolimus eluting stent, the present drug eluting stent can inhibit the intimal hyperplasia and the inflammatory reactions of vascular walls, and promote the endothelialization of blood vessels after the stent is implanted, and thus can prevent the long-term thrombotic complications; and has the advantages of small dosage, low cost, and no toxic side effect.

10 Claims, 2 Drawing Sheets

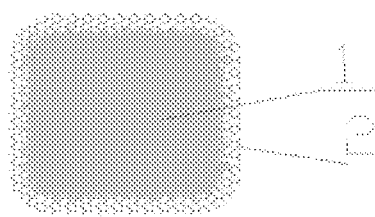
FIG. 1
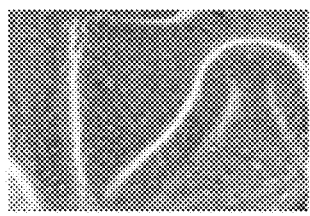   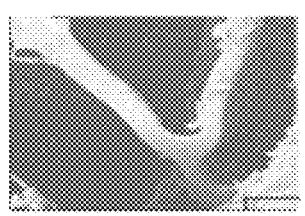   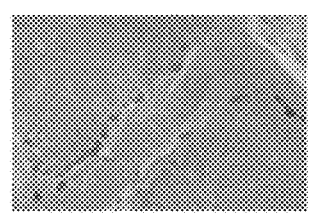
FIG. 2A          FIG. 2B          FIG. 2C
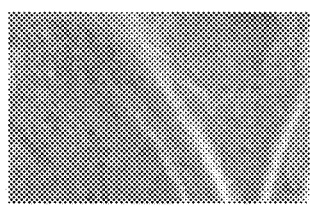   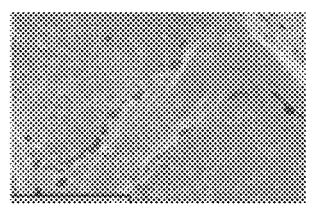   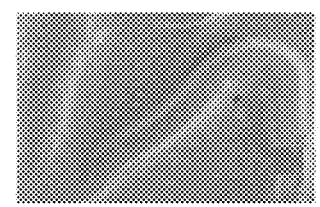
FIG. 3A          FIG. 3B          FIG. 3C
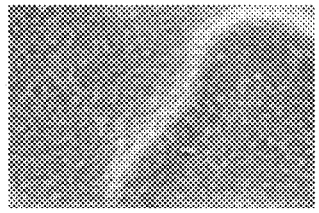   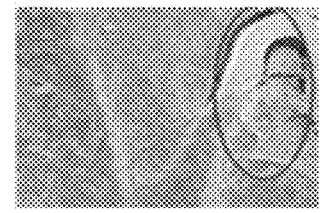   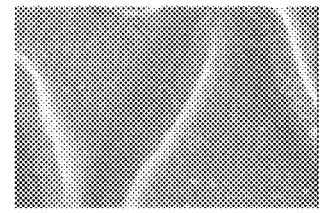
FIG. 4A          FIG. 4B          FIG. 4C

SCAFFOLD WITH DRUG COATING FOR TREATING RESTENOSIS AND PREPARATION METHOD THEREOF

RELATED APPLICATION

This application is a national phase entry under 35 USC 371 of International Patent Application No. PCT/CN2015/076946 filed on 20 Apr. 2013, which claims priority from Chinese Application No. 2014102325900 filed on 28 May 2014, the disclosures of which are incorporated in their entirety by reference herein.

BACKGROUND

Technical Field

The present invention relates to the technical field of medical apparatuses, and particularly to a stent with a drug coating for preventing and treating restenosis and a preparation method thereof.

Related Art

At present, percutaneous coronary intervention (PCI) is a main method for treating coronary heart disease. However, due to the unclear arteriosclerotic mechanism of the coronary arteries themselves and the potential damage caused by mechanical dilatation and implantation of a metal stent, the blood vessels locally produce an inflammatory reaction and excessive healing against the damage, leading to negative vascular remodeling, migration of smooth muscle cells, and neointimal hyperplasia. In-stent restenosis (ISR) is formed after PCI, and the restenosis rate can be up to 15 to 40% after the stent implantation.

In order to prevent the formation of restenosis, the previously developed drug-eluting stent (DES), also known as drug-releasing stent, is used to carry drugs by the polymer coated on the metal stent. When the stent is placed in the intravascular lesion, a biological effect is exerted by releasing the drug by means of elution from the polymer coating under control to the vascular wall tissue, whereby the restenosis rate after PCI is significantly reduced. DES is a new milestone in the development of PCI technology.

Effective stents commonly used in the prior art include, for example, sirolimus-, paclitaxel- and other drug eluting stents, which have a reliable therapeutic effect in the prevention of restenosis after coronary artery balloon dilatation. However, these drugs inhibit the healing of injured intimal of the blood vessels after balloon dilation, thus increasing the long-term thrombotic complications. Several clinical trials and meta-analysis show that such drug-eluting stents may increase the incidence of death or myocardial infarction (in-stent thrombosis), which affects the long-term prognosis. The annual incidence of cardiac events after PCI for acute myocardial infarction is about 20%, and the incidence of restenosis after implantation of a drug eluting stent is still about 10%. In addition, such drug-eluting stents are expensive, and an imported stent costs about 20,000 RMB, which is not suitable for generalization considering China's national conditions, due to the increased medical costs and financial burden of the patients.

In view of the pathophysiologic mechanism of restenosis, drug-eluting stents with anti-thrombotic, anti-inflammatory and anti-cell migration and proliferative effects theoretically have the effect of preventing restenosis. However, the results of research on use of these drug eluting stents after PCI are undesirable, because although the drugs can reduce restenosis, some have serious toxic and side effects.

SUMMARY

To overcome the disadvantages of drug eluting stents existing in the prior art, the present invention provides a stent with a drug coating for preventing and treating restenosis and a preparation method thereof. Compared with an existing sirolimus eluting stent, the present drug eluting stent can inhibit the intimal hyperplasia and the inflammatory reactions of vascular walls, and promote the endothelialization of blood vessels after the stent is implanted, and thus can prevent the long-term thrombotic complications; and has the advantages of small dosage, low cost, and no toxic side effect.

The present invention provides a stent with a drug coating for preventing and treating restenosis, which includes a stent and a drug coating covering the surface of the stent. The active ingredients in the drug coating are guaiane sesquiterpene compounds P1, P2 and P3, where P1 is Zedoalactone B having a structure formula of

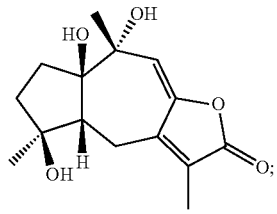 [SMILES: CC1=C2C[C@@H]3[C@@](C)(O)CC[C@]3(O)[C@](C)(O)C=C2OC1=O]

P2 is a stereoisomer of P1 having a structure formula of:

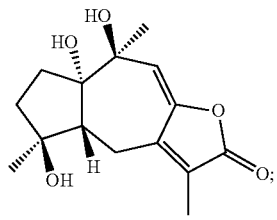 [SMILES: CC1=C2C[C@@H]3[C@@](C)(O)CC[C@@]3(O)[C@@](C)(O)C=C2OC1=O]

and

P3 is Zedoarondiol having a structure formula of

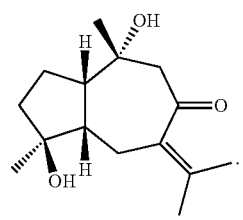 [SMILES: CC(C)=C1C[C@H]2[C@H](CC[C@]2(C)O)[C@](C)(O)CC1=O]

The weight ratio of the guaiane sesquiterpene compounds P1, P2, and P3 in the coated stent is P1:P2:P3=(16-64):(2.5-10):(25-100).

The weight ratio of the guaiane sesquiterpene compounds P1, P2, and P3 in the coated stent is P1; P2: P3=32:5:50.

The active ingredients in the drug coating have a drug load of 0.7-0.9 μg/mm² on the stent.

The stent is a stainless steel nanoporous stent.

A method for preparing the stent with a drag coating for preventing and treating restenosis comprises (1) dissolving a mixture of guaiane sesquiterpene compounds P1, P2, and P3 in a solvent, to formulate a drug solution, and then ultrasonicating the drug solution;

(2) evenly coating the drug solution onto the stent by spraying, and then freeze drying the stent in a freeze drier after being coated with the drag solution by spraying;

where the solvent is ultrapure water, and the mixture of the guaiane sesquiterpene compounds P1, P2, and P3 is formulated in the solvent in a proportion such that 100 mg of the drug solution contains 2.5 mg of the mixture;

(3) fitting the stent onto a pre-dilated balloon mated therewith; and (4) sterilizing the stent with oxirane after being fitted.

The present invention has the following effects.

(1) The stent provided in the present invention can inhibit the proliferation of vascular smooth muscle cells and the inflammatory reactions of vascular walls. Compared with existing drugs, the present stent can further promote the healing of vascular intimal, and prevent the long-term thrombotic complications.

(2) The compounds P1, P2, and P3 have known and definite structures, and can be extracted from naturally occurring traditional Chinese medicine *Rhizoma Curcumae*, thereby saving the production cost.

(3) The effect of preventing the occurrence of and treating restenosis can be achieved by using the stent of the present invention with a small drug load, which can not only reduce the cost, but also avoid the adverse effect brought about by a high dosage.

(4) Compared with an existing sirolimus eluting stent for preventing and treating restenosis, the present stent has no toxic side effect.

BRIEF DESCRIPTION OF THE DRAWINGS

FIG. 1 is a schematic cross-sectional structural view of a stent with a drug coating for preventing and treating restenosis provided in the present invention;

FIG. 2A is a scanning electron micrograph of a zotarolimus eluting stent (ZES) provided in the present invention at day 7 after implantation;

FIG. 2B is a scanning electron micrograph of a sirolimus eluting stent (SES) at day 7 after implantation;

FIG. 2C is a scanning electron micrograph of a bare-metal stent (BMS) at day 7 after implantation;

FIG. 3A is a scanning electron micrograph of a zotarolimus eluting stent (ZES) provided in the present invention at day 14 after implantation;

FIG. 3B is a scanning electron micrograph of a sirolimus eluting stent (SES) at day 14 after implantation;

FIG. 3C is a scanning electron micrograph of a bare-metal stent (BMS) at day 14 after implantation;

FIG. 4A is a scanning electron micrograph of a zotarolimus eluting stent (ZES) provided in the present invention at day 28 after implantation;

FIG. 4B is a scanning electron micrograph of a sirolimus eluting stent (SES) at day 28 after implantation;

FIG. 4C is a scanning electron micrograph of a bare-metal stent (BMS) at day 28 after implantation;

In the figures 1. metallic stent matrix: 2. drug coating

DETAILED DESCRIPTION

For better understanding of the technical solution of the present invention by those skilled in the art, the present invention is described in further detail below with reference to accompanying drawings and specific embodiments.

Figure 5:
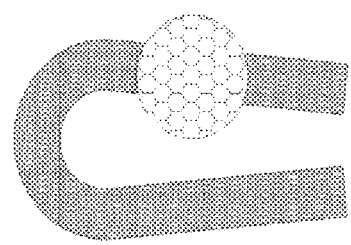
FIG. 5 is a schematic structural side view of a stent with a drug coating for preventing and treating restenosis provided in the present invention.
Figure 6:
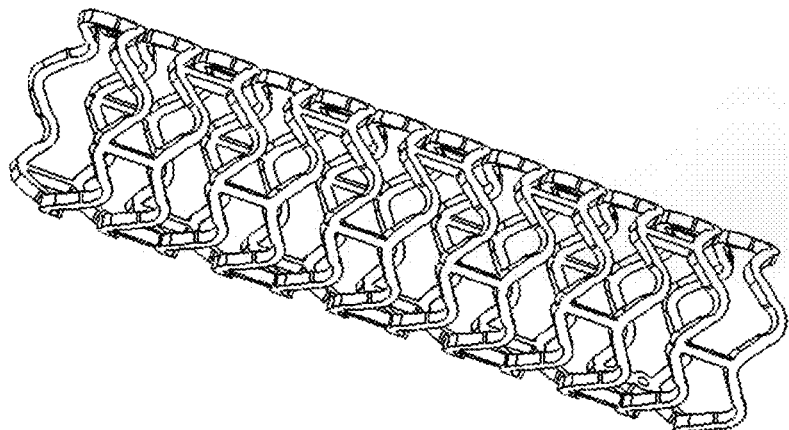
FIG. 6 is a schematic three-dimensional structural view of a stent with a drug coating for preventing and treating restenosis provided in the present invention.

Referring to FIG. 1, a stent with a drug coating for preventing and treating restenosis provided in the present invention includes a stent 1 and a drug coating 2 covering the surface of the stent. The stent is a nanoporous 316L stainless steel metal-bare stent supplied by Beijing Lepu Medical Device Inc. The side and three-dimensional structure of the stent may be made reference to FIGS. 5 and 6.

The active ingredients in the drug coating comprise

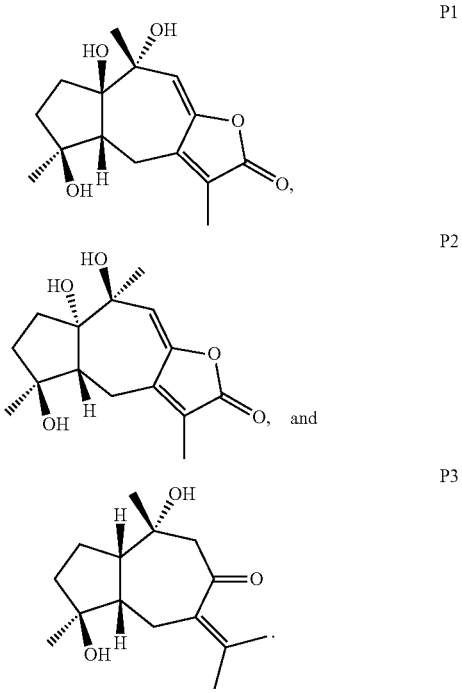

The compounds P1, P2, and P3 are all guaiane sesquiterpene compounds, in which P1 is Zedoalactone B, P2 is a stereoisomer of P1, and P3 is Zedoarondiol. The three compounds can be extracted from *Rhizoma Curcumae*, through a process including specifically the following.

1. Sample Pretreatment

Extraction: (1-10) Kg of *Rhizoma Curcumae* as a bulk powder is weighed and extracted in two batches. *Rhizoma Curcumae* is extracted three times by spinning for 2 hrs in 10 L of water at 95° C. The extracted sample solutions are combined and centrifuged, to obtain about 43.5 L of a centrifuged extract. 50 mL of each is reserved for analysis.

Separation by ultrafiltration: 43.5 L of the centrifuged extract is added to a liquid tank of a membrane separation apparatus and separated by ultrafiltration (hollow fiber membrane UF, model PS06, membrane area 4.0 M2, No. 09-0114), to obtain about 43 L of a ultrafiltration permeate (because water is not discharged thoroughly before ultrafiltration), and 3.5 L of a ultrafiltration retentate 50 mL of each is reserved for analysis.

Concentration by nanofiltration: 43 L of the ultrafiltration permeate is added to a nanofiltration apparatus which is adjusted to have a frequency of 20 Hz and a pressure at the liquid outlet of 0.5 MPa. 3.9 L of a nanofiltration retentate and 40.1 L of a nanofiltration permeate are obtained. 50 mL of each is reserved for analysis.

2. X1 Preparation (First-Dimensional Preparation) of Guaiane Sesquiterpene Compounds from *Rhizoma Curcumae*

The chromatographic column is activated with 3-fold column volumes of 95% ethanol, and then equilibrated with 2-fold column volumes of water. 1.9 L of the nanofiltrated solution is loaded, washed with water, repeatedly rinsed 5 times with 3-fold column volumes of 10%-50% ethanol, and eluted. The column is washed, and the fractions are combined to obtain sub-fractions F6, F7, F8, F9, F11, F12, and F16. The target main peaks are P1, P2, and P3.

3. Preparation by C18HC Column (Second-Dimensional Preparation) of Guaiane Sesquiterpene Compounds from *Rhizoma Curcumae*

Preparation of Peak P1

Sample formulation: 190 mg of *Rhizoma Curcumae* sample F6 is dissolved in 10 mL of water to give a concentration of about 20 mg/mL. 400 mg of samples F7-9 was dissolved in 20 mL of water, to give a concentration of about 20 mg/mL. Preparation conditions: chromatographic column: C18HC (20×250 mm, 10 m, No. 12041901A); flow rate: 20 mL/min, detector: 275 nm, 240 nm; and injected volume: 5 mL. The elution conditions for peak P1 are shown in Table 1.

TABLE 1

Elution conditions for the preparation of peak P1

| Time (min) | Flow rate | Percent by weight of methanol | Percent by weight of 0.2% formic acid in water |
|---|---|---|---|
| 0-35 | 20 mL/min | 14 | 86 |
| 35.1-40 | 20 mL/min | 90 | 10 |

Preparation of Peak P1 (Sample F11)

Sample formulation: 350 mg of *Rhizoma Curcumae* samples F11 and F12 is dissolved in 10 mL of water to give a concentration of about 35 mg/mL, and then filtrated through a hydrophilic membrane. Chromatographic column: C18HC (20×250 mm, 10 m, No. 12041901 A); flow rate: 20 mL/min; detector: 275 nm, 240 nm; and injected volume: 1 mL. Specific conditions are shown in Table 2.

TABLE 2

Elution conditions for the preparation of peak P2

| Time (min) | Flow rate | Percent by weight of methanol | Percent by weight of 0.2% formic acid in water |
|---|---|---|---|
| 0-35 | 20 mL/min | 14 | 86 |
| 35.1-40 | 20 mL/min | 90 | 10 |

Preparation of Peak P3 (Sample F16)

Sample formulation: 350 mg of *Rhizoma Curcumae* sample F16 is dissolved in 20 mL of water, to give a concentration of about 17 mg/mL, and then filtrated through a hydrophilic membrane. Chromatographic column: C18HC (20×250 mm, 10 m, No. 12041901A); flow rate: 20 mL/min; detector: 275 nm, 240 nm; and injected volume: 1 mL.

Specific conditions are shown in Table 3.

TABLE 3

Elution conditions for the preparation of peak P3

| Time (min) | Flow rate | Percent by weight of methanol | Percent by weight of 0.2% formic acid in water |
|---|---|---|---|
| 0-35 | 20 mL/min | 30 | 70 |
| 35.1-40 | 20 mL/min | 90 | 10 |

4. Purity Analysis and Structure Characterization of P1, P2, and P3

Chromatographic Purity Analysis:

Instrument: Alliance 6; chromatographic column: C18TDE (4.6×150 mm, 5 m, No. 110517-5), flow rate: 1 mL/min; detector: 275 nm, 240 nm; injected volume: 50 L; and elution condition: gradient elution. The gradient elution conditions are shown in Table 4.

TABLE 4

Preparative elution conditions for chromatographic purity analysis

| Time (min) | Percent by weight of acetonitrile | Percent by weight of 0.1% formic acid in water |
|---|---|---|
| 0 | 5 | 95 |
| 20 | 40 | 75 |
| 25-30 | 95 | 5 |

Structure characterization of P1, P2, and P3: 20 mg P1, 2.7 mg P2, and 25.5 mg P3 are obtained after elution. The results of purity analysis based on relative peak area show that the purity of P1 is 99.06%, the purity of P2 is 96.26%, and the purity of P3 is 98.44%.

It can be known through comparison with the nuclear magnetic resonance data in literatures that the three compounds are guaiane sesquiterpene compounds, where P1 is Zedoalactone B, P2 is a stereoisomer of P1, and P3 is Zedoarondiol.

32 mg, 5 mg, and 50 mg of the compounds P1, P2, and P3 are dissolved in ultrapure water, to prepare a 2.5 wt % drug solution of P1, P2, and P3 in admixture. The solution is ultrasonicated until the compounds P1, P2, and P3 are completely dissolved. The nanoporous 316L stainless steel stent matrix is cleaned with ultrapure water, and then the drug solution is coated onto the surface of the stent by spraying. Subsequently, the coated stent is freeze dried in a freeze drier. The freeze dried stent is removed and fitted onto a pre-dilated balloon mated therewith. Finally, the stent is sterilized with oxirane.

The nanoporous 316L stainless steel stent has a diameter of 2.5-4.0 mm, a surface area of 90±15 mm2, and a nominal drug load of 0.83 μg/mm2.

Test Example 1

Animal Experiment

1. Animals and grouping: 36 ordinary Chinese miniature pigs (supplied by China Agricultural University, female: male 1:1, body weight (25-30) kg) were randomized into a *Rhizoma Curcumae* extract eluting stent (ZES) group, a sirolimus eluting stent (SES) group, and a metal-bare stent (BMS) group, each group having 12 animals.

The ZES stent is a stent provided in Example 1 of the present invention, which is referred to as ZES stent since the compounds P1, P2, and P3 are all extracted from *Rhizoma Curcumae*. The SES stent is a sirolimus eluting Nanostent, which, together with the metal-bare stent (BMS), is supplied by Beijing Lepu Medical Device Inc., and has a stent matrix that is the same as that of the ZES stent and is nanoporous 316L stainless steel stent.

Experiment procedure: 3 days before operation, 300 mg aspirin and 50 mg clopidogrel were given daily. An intravenous path was established. The animals were weighed and anaesthetized by intramuscularly injecting pentobarbital at a dosage of 0.5 mg/kg and intravenously injecting ketamine at a dosage of 10 mg/kg in combination. Coronary angiography was performed as follows. The porcine femoral artery was punctured by Seldinger method and a 6F arterial sheath was placed, through which heparin was given at a dosage of 200 U/kg. Then selective coronary angiography was performed. The stents in the three groups were implanted into the coronary artery of Chinese miniature pigs, and the ECG was continuously monitored during operation. After operation, the animals were each bred in a single cage with general cereal feed, and observed. 100 mg aspirin and 50 mg clopidogrel were given once a day, until the end of the experiment. The endothelial coverage on the stent strut and the intimal hyperplasia were determined by scanning electron microscopy at different time points (days 7, 14 and 28) after various types of stents were implanted. In addition, intravascular scanning imaging by a lightlab optical coherence tomography (OCT) system was performed on day 28 after the stents were implanted. The diameters of the lumen and adventitia of blood vessel were determined and the diameter and area stenosis rates were calculated. The endothelial repair and stent thrombosis were qualitatively evaluated.

Experimental Results and Conclusions

1. Histopathological Observation

The observations on endothelial coverage on the stent strut and the intimal hyperplasia at different time points (days 7, 14 and 28) after various types of stents are implanted show that at day 7 after the stents are implanted, the stent strut is substantially covered with endothelial cells in the ZES group, followed by the coverage in the BMS group, and no endothelial coverage is observed on most of the stent struts in the SES group. At days 14 to 28, the stent strut is completely covered with endothelial cells in the ZES group, and no hyperintimal hyperplasia occurs; the endothelial coverage is complete in the BMS group, and there is obvious intimal hyperplasia, suggesting that the restenosis is severe in the section of the blood vessel where the stent resides; and some stent struts are still exposed in the SES group, indicating delayed endothelialization, as shown in FIG. 2.

Based on the above results, although the SES stent can significantly inhibit the proliferation and migration of smooth muscle cells (SMCs), the non-targeting characteristic leads to the inhibition on cycles of vascular endothelial cells, resulting in insufficient endothelial coverage and the risk of late stent thrombosis. The BMS stent cannot effectively inhibit the proliferation (migration) of SMCs, although the endothelial coverage can be realized with it, so in-stent restenosis become a prominent problem. In this study, it is found that the ZES stent can rapidly achieve the endothelial coverage (≤7 days) on the implanted stent in the shortest time, which confirms histologically that the ZES stent provided in the present invention promotes the growth of vascular endothelial cells while effectively inhibiting SMCs.

2. Evaluation by Optical Coherence Tomography (OCT)

It is found that at day 7 after the stents are implanted, the stent strut is substantially covered with new endothelial cells in the ZES group, no endothelial coverage is observed on stent struts in the SES group, and partial endothelial coverage is observed in the BMS group; at day 14, the stent struts are almost completely covered with new endothelial cells in the ZES and BMS groups, and the stent struts are partially covered with endothelial cells in the SES group; and at day 28, the stent struts are completely covered with new endothelial cells in the ZES group, part of the stent struts are uncovered in the SES group, and complete endothelial coverage and obvious in-stent restenosis are observed in the BMS group. No restenosis events occur in the ZES and SES groups. The comparison of morphologies by OCT on day 28 after the stents are implanted is shown in Table 1 below. Based on the above experimental results, it is concluded that the endothelial repair can significantly inhibit the infiltration of inflammatory factors, thereby reducing the stimulation of the inflammatory factors on the smooth muscle cells (SMCs) and reducing the proliferation and migration of SMC. In this way, the hypersensitive reaction induced from inflammation, poor stent adhesion to the wall in a later stage, positive reconstruction and others are solved radically. After the stent is implanted, the faster the endothelialization of the vascular walls is, the smaller the infiltration of inflammatory factors is, and the lower the opportunity to proliferation and migration of SMCs is. The above-mentioned technical effects can be totally achieved with the stent provided in the present invention.

Term explanation: ZES, SES, and BMS are respectively *Rhizoma Curcumae* extract eluting stent, sirolimus eluting stent, and metal-bare stent, VD is the reference diameter of the blood vessel, LD is the mean diameter of the blood vessel, EELD is the mean diameter of the adventitia, diameter stenosis is the diameter stenosis rate, LA is the mean area of the lumen, EELA is the mean area of the adventitia, and area stennosis is the area stennosis rate.

3. Effects on Liver and Kidney Function

Before and after the ZES stent is implanted, the blood specimens were collected and analyzed before and 30 days after the experiment. The results show that no obvious changes are found in the glutamic oxaloacetic transaminase (ALT) and glutamic pyruvic transaminase (AST) levels indicating the liver function of the experimental miniature pigs, and no obvious changes are found for the kidney function indices blood creatinine (Cr) and urea nitrogen (UA) levels before and after experiment, suggesting that under the experimental conditions, the drugs carried by the stent, i.e. the guaiane sesquiterpenoid compounds, have no obvious toxic side effect on the liver and kidney function of the experimental animals.

4. Quantified Evaluation for Restenosis, Microthrombi and Intimal Hyperplasia

The measurement results are shown in a table below.

TABLE 5

Comparison of integrated injury, area restennosis, and integrated microthrombi ($\overline{X} \pm S$) 30 days after the stents are implanted

| Group | Case number | Integrated injury integral | Area restenosis (%) | Integrated microthrombi |
|---|---|---|---|---|
| MBS group | 12 | 3.26 ± 0.73 | 0.49 ± 0.19 | 2.07 ± 0.46 |
| SES group | 12 | 2.93 ± 0.69 | 0.45 ± 0.23 | 0.99 ± 0.43 |
| ZES group | 12 | 2.16 ± 0.64*# | 0.38 ± 0.17 | 0.89 ± 0.39# |

Note:
compared with the SES group,
*$P < 0.05$; and compared with the MBS group,
$P < 0.05$.

TABLE 6

Comparison of degree of intimal hyperplasia 30 days after the stents are implanted ($\overline{X} \pm S$)

| Group | Case number | Area of intimal hyperplasia (A) | Area of the lumen (TA) | Percentage of intimal increase (%) |
|---|---|---|---|---|
| MBS group | 12 | 1.69 ± 0.13 | 4.14 ± 0.36 | 40.82 ± 1.36 |
| SES group | 12 | 0.63 ± 0.27* | 3.87 ± 0.29 | 16.27 ± 1.15* |
| ZES group | 12 | 0.57 ± 0.23* | 3.97 ± 0.31 | 14.35 ± 1.42* |

Note:
compared with the MBS group,
*$P < 0.05$, and
**$P < 0.01$.

It can be known from the measurement results in the table above that vascular endothelium plays an important role in terms of the efficacy of a stent for treating coronary atherosclerotic heart disease after being implanted. Endothelialization of intravascular stent is one of the effective ways to solve the problem of thrombosis and improve the long-term patency rate after stent implantation. The ZES stent can effectively reduce the inflammation of vascular endothelium, inhibit the intimal hyperplasia, reduce the intimal increase after stent implantation, and promote the vascular endothelialization.

Hereinbefore, the stent with a drug coating for preventing and treating restenosis and the preparation method thereof provided in the present invention are described in detail. The principles and embodiments of the present invention have been set forth by way of specific examples which are provided merely for promoting the understanding of the central idea of the present invention. It should be noted that modifications and variations may be made to the present invention by those skilled in the art without departing from the principles of the present invention, which all fall within the protection scope of the present invention as defined by the claims.

What is claimed is:

1. A stent with a drug coating for treating restenosis, comprising a stent and a drug coating covering the surface of the stent, wherein the active ingredients in the drug coating are guaiane sesquiterpene compounds P1, P2, and P3;

wherein P1 is Zedoalactone B having a structure formula of

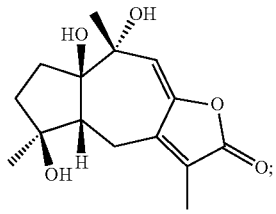 [SMILES: CC1=C2C[C@@H]3[C@@](C)(O)CC[C@]3(O)[C@](C)(O)C=C2OC1=O]

P2 is a stereoisomer of P1 having a structure formula of:

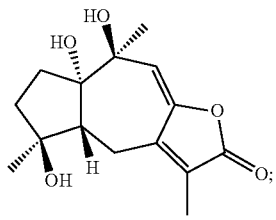 [SMILES: CC1=C2C[C@@H]3[C@@](C)(O)CC[C@@]3(O)[C@@](C)(O)C=C2OC1=O]

and
P3 is Zedoarondiol having a structure formula of

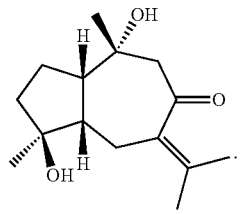 [SMILES: CC(C)=C1C[C@H]2[C@H](CC[C@]2(C)O)[C@](C)(O)CC1=O]

2. The stent with a drug coating for treating restenosis according to claim 1, wherein the drug coating comprises guaiane sesquiterpene compounds P1, P2, and P3 at a weight ratio of P1:P2:P3=(16-64):(2.5-10):(25-100).

3. The stent with a drug coating for treating restenosis according to claim 1, wherein the drug coating comprises guaiane sesquiterpene compounds P1, P2, and P3 at a weight ratio of P1:P2:P3=32:5:50.

4. The stent with a drug coating for treating restenosis according to claim 2, wherein the active ingredients in the drug coating have a drug load of 0.7-0.9 µg/mm² on the stent.

5. The stent with a drug coating for treating restenosis according to claim 1, wherein the stent is a stainless steel nanoporous stent.

6. A method for preparing the stent with a drug coating for treating restenosis according to claim 1, comprising:
   (1) dissolving a mixture of guaiane sesquiterpene compounds P1, P2, and P3 in a solvent, to formulate a drug solution; and
   (2) evenly coating the drug solution onto the stent by spraying.

7. The method for preparing the stent with a drug coating for treating restenosis according to claim 6, wherein the solvent is ultrapure water, and the mixture of the guaiane sesquiterpene compounds P1, P2, and P3 is formulated in the solvent in a proportion such that 100 mg of the drug solution contains 2.5 mg of the mixture.

8. The method for preparing the stent with a drug coating for treating restenosis according to claim 6, wherein the step (1) further comprises a process of ultrasonicating the drug solution.

9. The method for preparing the stent with a drug coating for treating restenosis according to claim 6, wherein the stent in step (2) is freeze dried in a freeze drier after being coated with the drug solution by spraying.

10. The method for preparing the stent with a drug coating for treating restenosis according to claim 6, further comprising sequentially
   (3) fitting the stent onto a pre-dilated balloon mated therewith; and
   (4) sterilizing the stent with oxirane after being fitted.

* * * * *